(12) United States Patent
Zolotoy et al.

(10) Patent No.: US 6,399,618 B1
(45) Date of Patent: Jun. 4, 2002

(54) COMPOSITIONS AND METHODS FOR MODULATING SEXUAL ACTIVITY

(75) Inventors: Alexander B. Zolotoy, Richmond; Eric S. Hayes, Victoria, both of (CA)

(73) Assignee: Cardiome Pharma Corp, Vancouver (CA)

( * ) Notice: Subject to any disclaimer, the term of this patent is extended or adjusted under 35 U.S.C. 154(b) by 0 days.

(21) Appl. No.: 09/111,684

(22) Filed: Jul. 8, 1998

Related U.S. Application Data

(60) Provisional application No. 60/052,051, filed on Jul. 9, 1997.

(51) Int. Cl.$^7$ ........................ A61K 31/495; A61K 31/50
(52) U.S. Cl. ........................... 514/255.01; 514/252.12; 514/252.01; 514/247
(58) Field of Search ................................ 514/255, 247, 514/252.01, 252.12, 255.01

(56) References Cited

U.S. PATENT DOCUMENTS

| | | | |
|---|---|---|---|
| 2,954,380 A | 9/1960 | Shapiro et al. | 260/268 |
| 4,150,137 A | 4/1979 | Noda et al. | 424/263 |
| 5,011,928 A | 4/1991 | Venero and Avello | 544/373 |
| 5,270,323 A | 12/1993 | Milne, Jr. et al. | 514/309 |
| 5,288,752 A * | 2/1994 | Tatsuoka et al. | 514/510 |
| 5,338,288 A * | 8/1994 | Finkle | 600/41 |
| 5,506,257 A | 4/1996 | MacLeod et al. | 514/422 |
| 5,637,583 A | 6/1997 | MacLeod et al. | 514/212 |
| 5,731,339 A | 3/1998 | Lowrey | 514/400 |
| 5,885,984 A | 3/1999 | MacLeod et al. | 514/211 |

FOREIGN PATENT DOCUMENTS

| | | |
|---|---|---|
| DE | 26 58 610 A1 | 7/1977 |
| EP | 357 581 B1 | 3/1990 |
| EP | 362 847 A2 | 4/1990 |
| EP | 432 199 B1 | 6/1991 |
| EP | 439 320 A1 | 7/1991 |
| EP | 459 377 A2 | 12/1991 |
| EP | 460 912 A2 | 12/1991 |
| EP | 608 511 A2 | 8/1994 |
| EP | 654 028 B1 | 5/1995 |
| EP | 702 555 B1 | 3/1996 |
| EP | 781 561 A1 | 7/1997 |
| EP | 812 845 A1 | 12/1997 |
| EP | 814 084 A1 | 12/1997 |
| JP | 53025533 | 3/1978 |
| WO | WO 94/28902 | 12/1994 |
| WO | WO 95/08544 | 3/1995 |
| WO | WO 99/02159 | 1/1999 |
| WO | WO 00/02550 | 1/2000 |

OTHER PUBLICATIONS

Suzuki et al., "Preparation and Pharmacological Evaluation of 1–(1,4–Benzoquinon–2–yl)–1,2,3,4–tetrahydronaphthalenes as Potent Cerebral Protective Agents," *Chem. Pharm. Bull.* 44(1): 132–138, 1996.

Tatsuoka et al., "Preparation and Pharmacological Evaluation of 4–(1,4–Benzoquinon–2–yl)–4–phenylbutanamides as Potential Cerebral Protective Agents," *Chem. Pharm. Bull.* 40(9): 2382–2386, 1992.

Berendsen et al., "Involvement of 5–HT $_{1C}$–Receptors in Drug–Induced Penile Erections in," *Psychopharmacology* 101: 57–61, 1990.

Biniecki and Horoskiewicz, "synthesis of 3–Indolylacetypiperazines and Reduction of Compounds Obtained with Lithium Aluminum Hydride," Database Chemabs Accession No. 84:59381 CA (& *Rocz. Chem.* 49(9): 1585–1588, 1975.

Bös et al., "Novel Agonists of 5HT–$_{2C}$ Receptors. Synthesis and Biological Evaluation of Substituted 2–(Indol–1–yl)–1–Methylethylamines and 2–(Indeno[1,2–b]pyrrol–1–yl)–1–methylethylamines. Improved Therapeutics for Obsessive Compulsive Disorder," *J. Med. Chem.* 40: 2762–2769, 1997.

Ceccarelli et al., "Synthesis ov Novel 2–Substituted–5–Oxycoumarans via A Direct Route to 2,3–Dihydro–5–Hydroxy–2–Benzofuranacetic Acids," *J. Heterocyclic Chem.* 30: 679–690, 1993.

de Costa et al., "Synthesis and Evaluation of Conformationally Restricted N–[2–(3,4–Dichlorophenyl)ethyl]–N–methyl–2–(1–pyrrolidinyl)ethylamines at σ Receptors. 2. Piperazines, Bicyclic Amines, Bridged Bicyclic Amines, and Miscellaneous Compounds," *J. Med. Chem.* 36: 2311–2320, 1993.

Fiorella et al., "The Role of the 5–HT$_{2A}$ and 5–HT$_{2C}$ Receptors in the Stimulus Effects of M–Chlorophenylpiperazine," Database Medline Accession No. 95388786 (& *Psychopharmacology* 119(2): 222–230, 1995.

Hayes et al., "Actions of Arylpiperazines on Corpus Cavernosum Smooth Muscle In Vitro," *Asia Pacific Journal of Pharmacology* 12: 97–103, 1997.

Hayes et al., "RSD 992 Enhances Erection and Copulation in Rats and Erection in Primates," *Int. J. Impot. Res.* 8(3), p. 189, abstract No. P24, 1996.

Hayes et al., "The Effects of 5HT Agonists on Central Peripheral and Local Erectile Pathways," *Int. J. Impot. Res.* 9(Suppl.), p. S34, abstract No. A8, 1997.

Millan et al., "5–HT$_{2C}$ Receptors Mediate Penile Erections in Rats: Actions of Novel and Selective Agonists and Antagonists," Database Medline Accession No. 97296368 (& *European Journal of Pharmacology* 325(1): 9–12, 1997.

Nortran Pharmaceuticals Internet Site. The Pro–Erectile Project. http://www.nortran.com/projects/PE.html. [Accessed Feb. 9, 2000].

(List continued on next page.)

*Primary Examiner*—Russell Travers
*Assistant Examiner*—Shengjun Wang
(74) *Attorney, Agent, or Firm*—Seed Intellectual Property Law Group PLLC

(57) ABSTRACT

The present invention discloses that a substituted acetic acid derivatives containing a N-alkylpiperazino moiety are useful as pro-libido agents for males and females, and may be used for the treatment of sexual dysfunction including impotence and to enhance sexual performance.

15 Claims, No Drawings

OTHER PUBLICATIONS

Sauter et al., "N–Substituierte Benzo[b]thiophen030acetamide and 3–(β–Aminoäthyl)–benzo[b]thiophene," *Monatsh. Chem.* 98(5): 2089–2096, 1967.

Hayes et al., "Direct Actions Of Arylpiperazines On Rabbit And Human Corpus Cavernosal Smooth Muscle In Vitro," at *International Symposium On Muscle Pharmacology*, Sinapore, May 9–10, 1997, P6.

Prasad et al., "Potential Antihypertensive Agents. II. Unsymmetrically 1,4–Disubstituted Piperazines. I," *J. Med. Chem.* 11(6): 1144–1150, 1968.

Hayes et al., "RSD 992 Enhances Erection And Copulation In Rats And Erection In Primates," *Int. J. Impot. Res.* 8(3): p. 189, Abstract No. P24, 1996.

Vadodaria et al., "Synthesis and Central Nervous System Depressant Activity of New Piperazine Derivatives and Related Compounds. II," *J. Med. Chem.* 12: 860–865, 1969.

Zikolova and Naumova, "Synthesis Of Piperazine Derivatives XI. Preparation Of $N^1$–Substituted $N^4$–Acyl Piperazines," *Tr. Nauchoizsled. Khim–Farm. Institute 9*: 105–113, 1974.

* cited by examiner

COMPOSITIONS AND METHODS FOR MODULATING SEXUAL ACTIVITY

This application claim benefit to provisional No. 60/052,051 filed Jul. 9, 1997.

TECHNICAL FIELD

The present invention is generally directed to N-alkylpiperazino derivatives of substituted acetic acids and pharmaceutical compositions thereof, to the preparation of such compounds and compositions, and to the use of such compounds and compositions to enhance sexual performance, as pro-libido agents and/or for the treatment and/or prevention of sexual dysfunction in male and/or female animals.

BACKGROUND OF THE INVENTION

At the present time there is a wide variety of pharmacological agents used and/or reportedly useful as pro-libido agents and/or for the treatment of sexual dysfunction. Some examples include: serotonin receptor agonists and antagonists (see, e.g., EP 385,658; WO 94/15,920; GB 2,248,449; and GB 2,276,165), dopamine receptor agonists (see, e.g., WO 93/23,035; WO 94/21,608; Pomerantz S. M., Pharmacol. *Biochem. Behav.* 39:123–128, 1991; and Ferrari F. et al. *Psychopharmacology* 113:172–176, 1993); adrenergic receptor agonists (see, e.g., WO 95/13,072; EP 611,248; U.S. Pat. No. 5,229,387; and WO 92/11,851); inhibitors of phoshodiesterase (see, e.g., DE 4,338,948; and WO 94/28,902); histamine receptor agonists (see, e.g., U.S. Pat. Nos. 4,013,659; 4,126,670; 4,767,778; WO 91/17,146; U.S. Pat. No. 5,047,418; and EP 0,458,661); neuropeptide Y antagonists (see, e.g., WO 95/00,161); angiotensin II receptor antagonists (see, e.g., EP 577,025); cholinesterase inhibitors (see, e.g., U.S. Pat. Nos. 5,177,070; and 4,633,318); combinations of agents with the different types of biological activity (see, e.g., U.S. Pat. No. 5,145,852; and WO 95/05,188); derivatives of vasoactive intestinal peptide (see, e.g., U.S. Pat. No. 5,147,855; EP 540,969; and EP 463,450); prostaglandins (see, e.g., WO 93/00,894; and EP 459,3770); antidepressants and antipsychotics (see, e.g., U.S. Pat. No. 4,931,445; GB 2,448,449; and Naganuma et al. *Clin. Exp. Pharm. Physiol.* 20:177–183, 1993); nitric oxide donors (see, e.g., WO 92/21,346; DE 4,305,881; DE 4,212,582; and WO 94/16,729); calcitonin gene related peptide (see, e.g., Steif, C. G. et al., *Urology*, 41:397–400, 1993); and androgens (see, e.g., JP 06,211,675; HU 62,473; and WO 94/16,709).

Many or all of these pharmacological agents are associated with adverse effects, some examples of which are quoted below. Dopamine receptor agonists may aggravate schizophrenia or induce it de novo in some patients. Serotonin receptor agonists are capable of producing an effect that has been termed "serotonin syndrome" (Glennon, R. A. *J. Med. Chem.* 30:1–9,1987). This latter effect has been thoroughly investigated in animals (Peroutka, S. J. *Science* 212:827–829, 1981; Goddwin G. M. et al., *Br. J. Pharmacol.* 84:743–753, 1985; and Tricklebank, M. D., *Eur. J. Pharmac.* 117:15–24, 1985) and manifests itself in, for example, head twitches, "wet dog shakes", forepaw treading, flat body posture, hind limb abduction, Straub tail and yawning. Histamine receptor agonists may induce central nervous system dysfunction and adverse effects in the endocrine system. Smooth muscle relaxants (such as papaverine) may induce pain, echytomosis and occasional episodes of priapism. α-Adrenoreceptor blockers administered systemically have been reported to induce priapism characterized by a persistent erection that cannot be relieved by sexual intercourse or masturbation (Kaisary, A. V. et al., *Br. J. Urol.* 68:227, 1986).

Accordingly there is a need in the art to identify new pharmacological agents, compositions and/or treatments which are useful as pro-libido agents and/or are useful in the treatment and/or prevention of sexual dysfunction in males or females, and/or can enhance a patient's sexual performance. The present invention fulfills these needs and further provides related advantages.

SUMMARY OF THE INVENTION

Briefly, one aspect of the invention provides compounds of formula (I)

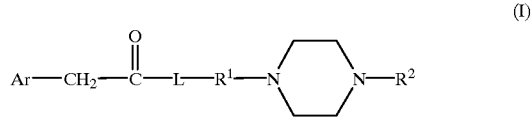

(I)

including salts, solvates, isolated enantiomers, isolated diastereomers, isolated tautomers, and mixtures thereof, wherein, independently at each occurrence:

Ar is selected from a $C_3$–$C_{13}$ carbocyclic ring, and ring systems selected from formulae (II), (III), (IV), (V), (VI), and (VII):

(II)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl;

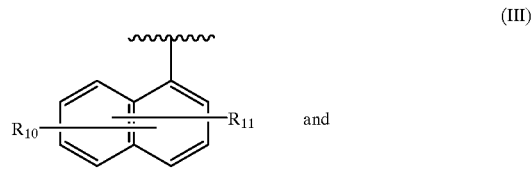

(III)

and

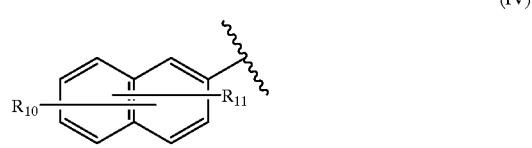

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15}, R_{16})$ where $R_{15}$ and $R_{16}$ are independently selected from hydrogen, acetyl, methanesulfonyl, and $C_1$–$C_6$alkyl;

(V)

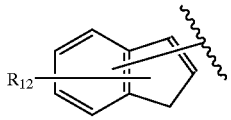

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15}, R_{16})$ where $R_{15}$ and $R_{16}$ are independently selected from hydrogen, acetyl, methanesulfonyl, and $C_1$–$C_6$alkyl;

(VI)

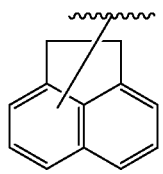

(VII)

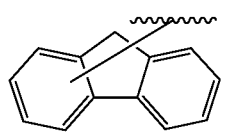

including isolated enantiomeric, diastereomeric, tautomeric and geometric isomers thereof, and mixtures thereof;

L is selected from the group of a direct bond, O, NH, and $N(C_1$–$C_6$ alkyl);

$R^1$ is selected from the group of a direct bond, a $C_1$–$C_6$ alkylene group, (such as —$CH_2$— and —$CH_2CH_2$—), and 1,2-disubstituted $C_5$–$C_6$ cycloalkyl; and $R^2$ is $C_1$–$C_6$ alkyl.

Another aspect of the invention provides pharmaceutical compositions comprising a pharmaceutically acceptable carrier or diluent in combination with a compound of formula (I):

(I)

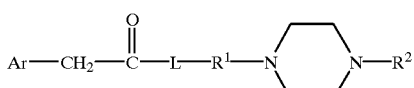

including salts, solvates, isolated enantiomers, isolated diastereomers, isolated tautomers, and mixtures thereof, having the definition set forth above.

Another aspect of the invention provides a method for treating and/or preventing sexual dysfunction in a male or female patient, where the method includes the step of administering to the patient in need thereof an amount of a compound of formula (I) or composition therefrom, (I)

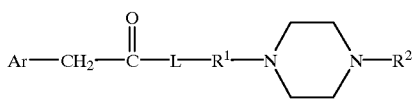

including salts, solvates, isolated enantiomers, isolated diastereomers, isolated tautomers, and mixtures thereof, having the definition set forth above, and where the amount is effective to treat and/or prevent the sexual dysfunction. The sexual dysfunction may be, for example, male erectile dysfunction or impotence.

Another aspect of the invention provides a use of a compound for manufacture of a medicament for treating and/or preventing sexual dysfunction in a male or female patient, wherein the compound is of formula (I)

(I)

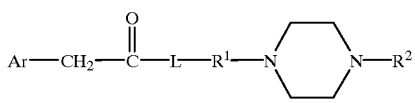

including salts, solvates, isolated enantiomers, isolated diastereomers, isolated tautomers, and mixtures thereof, which has the definition set forth above. The sexual dysfunction may be, for example, male erectile dysfunction or impotence.

Another aspect of the invention provides a method for increasing the libido of a male or female patient, where the method includes the step of administering to a male or female in need thereof an effective amount of a compound, or composition therefrom, of formula (I)

(I)

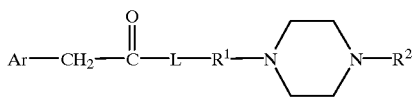

including salts, solvates, isolated enantiomers, isolated diastereomers, isolated tautomers, and mixtures thereof, which has the definition set forth above, and where the amount is effective to increase the libido of the patient.

Another aspect of the invention provides a use of a compound, or composition therefrom, for manufacture of a medicament for increasing the libido of a male or female patient, wherein the compound is of formula (I)

(I)

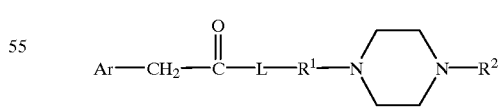

including salts, solvates, isolated enantiomers, isolated diastereomers, isolated tautomers, and mixtures thereof, which has the definition set forth above.

Another aspect of the invention provides a method for enhancing the sexual performance of a male or female patient, comprising administering to the patient in need thereof a therapeutically effective amount of a compound, or composition therefrom, of the formula (I)

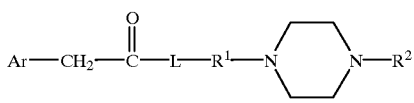
(I)

including salts, solvates, isolated enantiomers, isolated diastereomers, isolated tautomers, and mixtures thereof, which has the definition set forth above, and wherein the amount increases the sexual performance of the patient.

Another aspect of the invention provides a use of a compound, or composition therefrom, for manufacture of a medicament for enhancing the sexual performance of a male or female patient, wherein the compound is of formula (I)

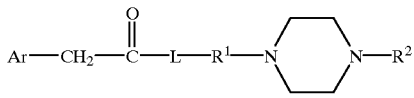
(I)

including salts, solvates, isolated enantiomers, isolated diastereomers, isolated tautomers, and mixtures thereof, which has the definition set forth above.

Another aspect of the invention is a method for the preparation of a compounds of formula (I)

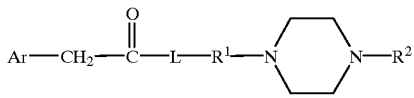
(I)

including salts, solvates, isolated enantiomers, isolated diastereomers, isolated tautomers, and mixtures thereof, having the definition set forth above. According to the inventive method, a substituted acetic acid compound or activated version thereof having the formula.

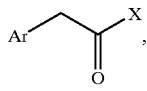

wherein X is OH or an activated (leaving) group such as chloride, is reacted with a compound having the formula

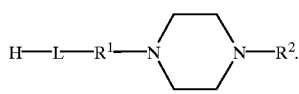
(I)

The reaction provides a bond between C=O and L as shown in formula

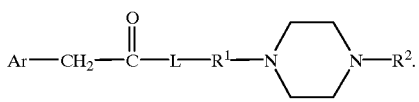
(I)

These and other aspects of the invention will be more fully understood upon reference to the following detailed description and examples.

DETAILED DESCRIPTION OF THE INVENTION

An understanding of the present invention may be aided by reference to the following definitions and explanation of conventions used herein.

Definitions and Conventions

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

In those instances where the invention specifies that a non-aromatic ring is substituted with more than one R group, and those R groups are shown connected to the non-aromatic ring with bonds that bisect ring bonds, then the R groups may be present at different atoms of the ring, or on the same atom of the ring, so long as that atom could otherwise be substituted with a hydrogen atom.

Likewise, where the invention specifies compounds containing the Ar—$CH_2C(O)$—L— group where Ar equals the group (V)

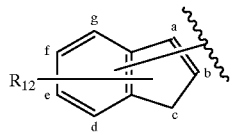
(V)

the invention is intended to encompass compounds wherein —$CH_2C(O)$—L— is joined through $CH_2$ to the Ar group (V) at any atom which forms the group (V) so long as that atom of group (V) could otherwise be substituted with a hydrogen atom. Thus, there are seven positions (identified with the letters "a" through "g") in structure (V) where the —$CH_2C(O)$—L— group could be attached, and it is attached at one of those seven positions. The $R_{12}$ group would occupy one and only one of the remaining six positions, and hydrogen atoms would be present in each of the five remaining positions.

The compounds of the present invention may contain two or more asymmetric carbon atoms and thus exist as enantiomers and diastereomers. Unless otherwise noted, the present invention includes all enantiomeric and diastereomeric forms of the compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers with all isomeric forms being included in the present invention. A racemate or racemic mixture does not imply only a 50:50 mixture of stereoisomers. The compounds of formula (I) may also exist in tautomeric forms and the invention includes both mixtures and separate individual tautomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents and/or variables are permissible only if such combinations result in stable compounds.

In accordance with the present invention and as used herein, the following terms are defined to have following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p- toluenesulfonic acid, salicylic acid and the like.

"Acyl" refers to branched or unbranched hydrocarbon fragments terminated by a carbonyl —(C=O)— group containing the specified number of carbon atoms. Examples include acetyl [$CH_3C$=O—, a $C_2$acyl] and propionyl [$CH_3CH_2C$=O—, a $C_3$acyl].

"Alkanoyloxy" refers to an ester substituent wherein the ether oxygen is the point of attachment to the molecule. Examples include propanoyloxy [($CH_3CH_2C$=O—O—, a $C_3$alkanoyloxy] and ethanoyloxy [$CH_3C$=O—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2OC$=O—, a $C_3$alkoxycarbonyl] and methoxycarbonyl [$CH_3OC$=O—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment substituted with an hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

As used herein, the term patient refers to a warm-blooded animal such as a mammal which can and will benefit from the above treatment (curative or prophylactic). It is understood that guinea pigs, dogs, cats, rats, mice, horses, cattle, sheep, and humans are examples of male and female patients within the scope of the meaning of the term.

"Pharmaceutically acceptable carriers" for therapeutic use are well known in the pharmaceutical art, and are described, for example, in *Remingtons Pharmaceutical Sciences,* Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of formula (I)" encompass compositions that contain more than one compound of formula (I).

Compounds of the Present Invention

As noted above, the present invention is directed toward compounds having formula (I)

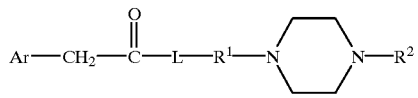

(I)

including salts, solvates, isolated enantiomers, isolated diastereomers, isolated tautomers, and mixtures thereof. In the compounds, independently at each occurrence:

Ar is selected from a $C_3$–$C_{13}$carbocyclic ring, and ring systems selected from formulae (III), (IV), (V), (VI), (VII) and (VIII), wherein compounds having each of the ring systems represented by formulae (II), (III), (IV), (V), (VI), and (VII) independently represent preferred sets of compounds of the invention:

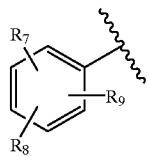

(II)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$—$C_6$alkyl;

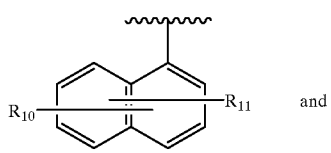

(III)

and (IV)

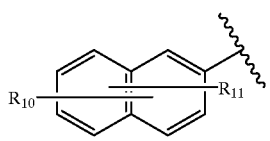

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

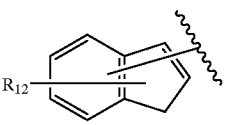

(V)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and

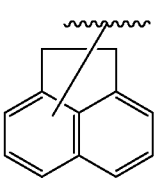

(VI)

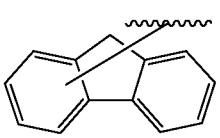

(VII)

including isolated enantiomeric, diastereomeric, tautomeric, and geometric isomers thereof, and mixtures thereof;

L is selected from the group of a direct bond, O, NH, and $N(C_1$–$C_6$ alkyl);

$R^1$ is selected from a direct bond, a $C_1$–$C_6$ alkylene group (such as —$CH_2$— and —$CH_2CH_2$—), and 1,2-disubstituted $C_5$–$C_6$ cycloalkyl; and $R^2$ is $C_1$–$C_6$ alkyl.

These compounds may be collectively referred to herein as "compounds of the invention" or "the inventive compounds" or "substituted acetic acid derivatives of the invention", or the like. In a preferred embodiment, Ar is an aryl group.

In general, compounds of the present invention may be in the form of a solvate or salt, preferably a pharmaceutically acceptable solvate or salt, e.g., an acid addition salt. Such salts include, without limitation, hydrochloride, sulfate, phosphate, citrate, fumarate, methanesulphonate, acetate, tartrate, maleate, lactate, mandelate, salicylate, succinate and other salts known in the art.

The Ar group is preferably but not necessarily a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_3$–$C_{13}$carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (II), (III), (IV), (V), (VI), or (VII) respectively.

A suitable Ar group within the compounds of the present invention is a phenyl ring represented by formula (II):

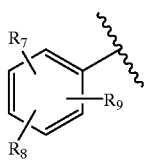

(II)

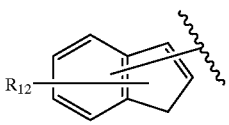

(V)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl.

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl.

Another suitable Ar group in compounds of the present invention is the acenaphthyl group as represented by formula (VI):

Other suitable Ar groups in compounds of the present invention are 1-naphthyl groups as represented by formula (II):

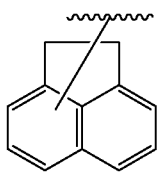

(VI)

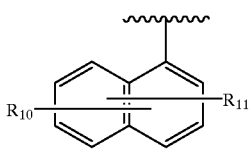

(III)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl.

Still another suitable Ar group in compounds of the present invention is the fluorenyl group as represented by formula (VII):

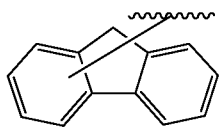

(VII)

In further preferred embodiments, the acenaphthyl group is a 1-acenaphthyl group, and the fluorenyl group is a 9-fluorenyl group.

Other suitable Ar groups in compounds of the present invention are 2-naphthyl group as represented by formula (IV):

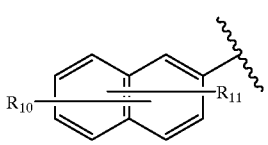

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl, as defined above.

In preferred embodiments of the invention, L is O, or NH, or $N(C_1$–$C_6$alkyl). $N(C_1$–$C_6$alkyl) refers to an alkyl-substituted N (nitrogen) atom, where the alkyl group has at least one and no more than six carbon atoms. These carbon atoms may be arranged in any linear, branched or cyclic fashion. Exemplary alkyl groups encompassed by $C_1$–$C_6$ alkyl include, without limitation, methyl, ethyl, n-propyl, iso-propyl, n-butyl, t-butyl, sec-butyl, t-butyl, cyclopropyl and cyclobutyl, cyclopentyl, methyl-substituted cyclopentyl (all isomers), and cyclohexyl, to name a few. A preferred alkyl group which may be bonded to the nitrogen atom is methyl.

In other preferred embodiments of the invention, for each of L being O (oxygen), NH or $N(C_1$–$C_6$alkyl), $R^1$ is a direct bond, or a $C_1$–$C_6$ alkylene group, or a 1,2-disubstituted $C_5$-cycloalkyl (i.e., 1,2-disubstituted cyclopentyl ring) or a 1,2-disubstituted $C_6$-cycloalkyl (i.e., 1,2-disubstituted cyclohexyl ring). In another preferred embodiment, compounds of the invention have L and $R^1$ both being direct bonds. In other preferred embodiments, $R^2$ is methyl for each of the compounds having L being O, NH or $N(C_1$–$C_6$alkyl), and $R^1$ being 1,2-disubstituted $C_6$-cycloalkylene, or 1,2-disubstituted $C_5$-cycloalkylene, or $C_1$–$C_6$alkylene.

Other suitable Ar groups in compounds of the present invention are aromatic groups represented by formula (V):

The $C_1$–$C_6$alkylene group has at least one, and as many as six carbon atoms. These carbon atoms may be arranged in a linear or branched fashion, so long as the carbon atoms have two open valencies for bonding to L and one nitrogen of the piperazino moiety. Exemplary $C_1$–$C_6$alkylene groups include, without limitation, —$CH_2$—, —$CH_2CH_2$—, —CH($CH_3$)$CH_2$—, and —$CH_2CH_2CH_2CH_2CH(CH_3)$—, which illustrate both linear and branched arrangements, and the lower end ($C_1$) and the upper end ($C_6$) of the alkylene chain.

In a preferred embodiment, the compounds of the invention have the formula

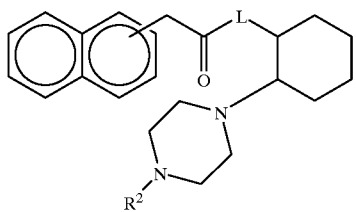

including salts, solvates, isolated enantiomers, isolated diastereomers, isolated tautomers, and mixtures thereof. In this formula, the bond joining the Ar group (naphthyl group) to the sidechain (—$CH_2$—C(=O)—L—etc.) is shown between two carbon atoms of the Ar group (rather than being connected to any one particular ring atom), to thereby denote that the sidechain may be joined to the Ar group at any position thereof.

In other preferred embodiments, a compound of the invention has the following formula

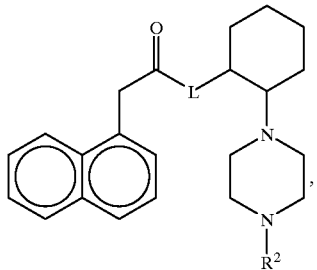

including salts, solvates, isolated enantiomers, isolated diastereomers, isolated tautomers, and mixtures thereof. According to this embodiment of the invention, a preferred compound has L equal to N($CH_3$), and is referred to herein as compound XVa (which encompasses both trans enantiomers). Also according to this embodiment, another preferred compound has L equal to O, and is referred to herein as compound XVc, where compound XVc includes both trans enantiomers.

In other preferred embodiments, the compound of the invention has the formula

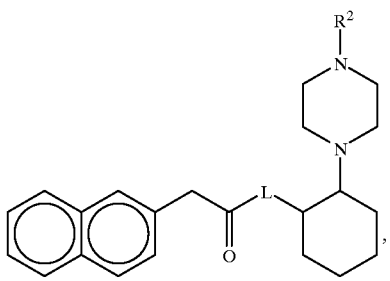

including salts, solvates, isolated enantiomers, isolated diastereomers, isolated tautomers, and mixtures thereof. According to this embodiment of the invention, a preferred compound has L equal to N($CH_3$), and when both enantiomers are present, is referred to herein as compound XVb.

In another preferred embodiment of compounds of the invention, when $R^1$ is a direct bond, then L is also a direct bond. Thus, preferred compounds of the invention have the formula

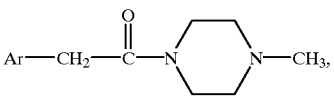

including salts, solvates, isolated enantiomers, isolated diastereomers, isolated tautomers, and mixtures thereof. According to this embodiment of the invention, a preferred compounds has Ar equal to 1-naphthyl, and is referred to herein as compound XVIa, and has the following structure

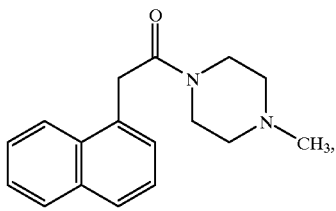

including salts, solvates, isolated tautomers, and mixtures thereof.

Also according to this embodiment of the invention, another preferred compounds has Ar equal to 2-naphthyl, and is referred to herein as compound XVIb, and has the following structure

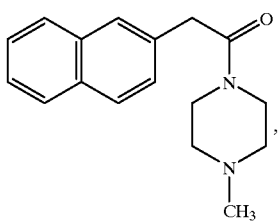

including salts, solvates, and mixtures thereof.

In another embodiment, the compound has one of the following formulas

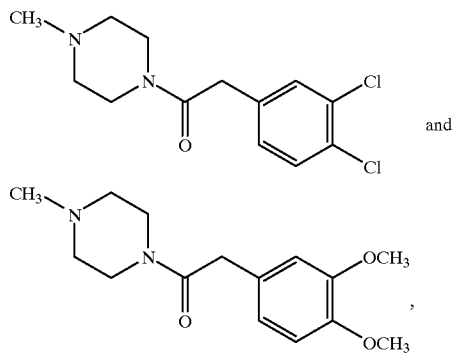

including salts, solvates, isolated tautomers, and mixtures thereof.

Certain compounds of the invention may be prepared by a method wherein a substituted acetic acid compound or activated version thereof, having the formula

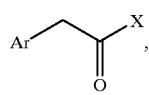

wherein X is OH or an activated (leaving) group such as chloride, is reacted with a compound of the formula

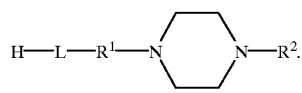

The reaction provides a bond between C=O and L as shown in the formula

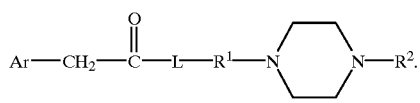

Compounds of formula Ar—CH$_2$—C(=O)—X, wherein X is other than —OH, may be prepared from the corresponding acid (where X is —OH). These acid starting materials, such as 1-naphthalene acetic acid, 2-naphthalene acetic acid, phenylacetic acid, bromophenylacetic acid (including the 2-, 3- and 4-positional isomers), methylphenylacetic acid (also known as tolylacetic acid) and many other compounds of the formula Ar—CH$_2$—COOH are commercially available. See, e.g., Aldrich Chemical Co., Milwaukee, Wis.

A substituted acetic acid may be reacted with, e.g., thionyl chloride, to prepare an activated substituted acetic acid compound. Other synthetic protocols for preparing an activated acid may be found in, e.g., Szmuszkovicz, J.; Von Voigtlander, P. F. (1982) *J. Med. Chem.* 25: 1125–1126; U.S. Pat. No. 5,506,257 to MacLeod B. A. et al., U.S. Pat. No. 5,637,583 to MacLeod B. A. et al. and Clark, C. R. et al. (1988) *J. Med. Chem.* 31: 831–836.

The activated substituted acetic acid compound is then reacted with an amine or alcohol compound (depending on the identity of L) of the formula

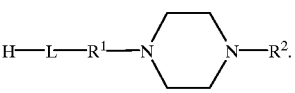

The preparation of 1,2-diaminocyclohexyl intermediates is described in, e.g., Szmuszkovicz, J.; Von Voigtlander, P. F. (1982) *J. Med. Chem.* 25: 1125–1126; and U.S. Pat. No. 5,506,257 to MacLeod B. A. et al. The preparation of 1-hydroxy-2-aminocyclohexyl intermediate is described in U.S. Pat. No. 5,637,583, also to MacLeod B. A. et al. The preparation of reactive carboxylic acid derivatives is described in the above references as well as in Clark, C. R. et al. (1988) *J. Med. Chem.* 31: 831–836.

The carboxylic acids may be coupled to the amine in the presence of a coupling reagent such as dicyclohexyl carbodiimide (DCC) or the like. The reaction is generally carried out in a suitable solvent such as tetrahydrofuran or dioxane at ambient temperature, but depending upon the reactivity of the specific starting materials employed, the reaction time, solvent employed and reaction temperature may be varied without undue experimentation by one of ordinary skill in the art, to achieve the desired coupling reaction. A reaction temperature of between about –25° C. and the boiling point of the solvent are typically employed. The reaction between the activated carboxylic acid (e.g., acid chloride) and the amine is generally carried out at ambient temperature in a suitable solvent such as chloroform or dichloromethane in the presence of an acid acceptor (i.e., base) such as a tertiary amine or an alkaline metal carbonate or bicarbonate. The mixture of amine and acid halide is allowed to react until the reaction is essentially complete.

Compositions of the Present Invention

The present invention provides compositions, preferably pharmaceutical compositions, which contain at least one compound of the present invention as set forth above, and at least one pharmaceutically acceptable carrier or diluent, where the compounds of the present invention have formula (I)

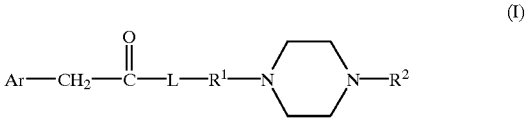

(I)

including salts, solvates, isolated enantiomers, isolated diastereomers, isolated tautomers, and mixtures thereof, wherein, independently at each occurrence:

Ar is selected from a $C_3$–$C_{13}$ carbocyclic ring, and ring systems selected from formulae (II), (III), (IV), (V), (VI), and (VII):

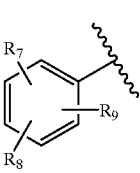

(II)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl;

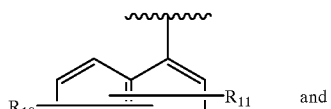

(III)

and

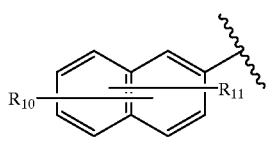

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

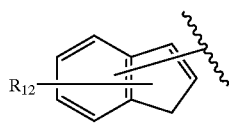

(V)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and

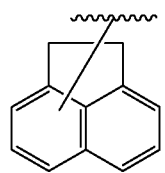

(VI)

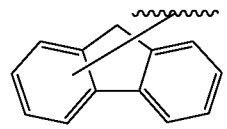

(VII)

including isolated enantiomeric, diastereomeric, tautomeric, and geometric isomers thereof, and mixtures thereof;

L is selected from the group of a direct bond, O, NH, and $N(C_1$–$C_6$ alkyl);

$R^1$ is selected from the group of a direct bond, a $C_1$–$C_6$ alkylene group, and a 1,2-disubstituted $C_5$–$C_6$ cycloalkyl; and $R^2$ is $C_1$–$C_6$ alkyl.

The composition may include, for example, water. In a preferred embodiment, the composition is in the form of a tablet, and particularly a fast-release tablet for oral administration. A fast-release tablet (having a rapid disintegration time) is desired in order to provide the patient with a rapid onset of enhanced sexual performance and/or increased libido and/or relief of sexual dysfunction.

A "fast-release" tablet will have a disintegration time of less than about one hour, preferably less than about 20 minutes, and more preferably less than about two or even one minutes. A suitable fast-release tablet contains 40 mg of a compound of the present invention, 8 mg of silicon dioxide (NF), 4 mg of stearic acid (NF), 212 mg of lactose (NF), 120 mg of microcrystalline cellulose (NF) and 16 mg of croscarmellose sodium (NF). A tablet containing these ingredients may be prepared by finely dividing and then mixing each ingredient together, then compressing the mixture into a tablet form. The tablet has a weight of about 400 mg. Other methods of mixing and tablet formulation will be readily apparent to one of ordinary skill in the art. A tablet prepared by this method will typically have a hardness of 10.7 Kp, an average thickness of about 0.2 inches and an average disintegration time of about 45 minutes.

Disintegrant compounds, such as croscarmellose sodium (NF) (available as Ac-Di-Sol from FMC Corporation), may be used to enhance the dissolution time of a formulation of the present invention. Other disintegrants such as potato starch, Explotab™ sodium starch glycolate, Polyplasdone™ XL crospovidone NF, Starch 1500™ pregelatinized starch NF may be employed in the formulations of the present invention. Each of U.S. Pat. Nos. 5,731,339, 5,298,261 and 5,079,018 also describe formulations which demonstrate fast disintegration times, which may be employed to prepare a fast release formulation of the present invention.

Suitable disintegrants and methods for measuring disintegration time of tablets include Gissinger et al. "A Comparative Evaluation of the Properties of some Table Disintegrants" *Drug Development and Industrial Pharmacy* 6(5) :511–536 (1980); and *European Pharmacopeia* 1980.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrameatal, intraurethral injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred composition contain, in addition to the inventive compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the inventive compound. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The compounds of the invention may be administered through use of insert(s), bead(s), timed-release formulation (s), patch(es) or fast-release formulation(s).

It will be evident to those of ordinary skill in the art that the optimal dosage of the substituted acetic acid derivatives of the invention may depend on the weight and physical condition of the patient; on the severity and longevity of the sexual dysfunction (when the goal is to treat sexual dysfunction); on the particular form of the active ingredient, the manner of administration and the composition employed. It is to be understood that use of a substituted acetic compound of the invention in a chemotherapy can involve such a compound being bound to an agent, for example, a monoclonal or polyclonal antibody, a protein or a liposome, which assist the delivery of said compound.

Therefore, the invention relates further to a pharmaceutical or veterinary composition comprising an effective amount of a substituted acetic acid derivative of formula (I) provided above, in association with a carrier.

In a further embodiment, the present invention is directed to the use of a substituted acetic acid derivative of the formula provided above (which includes physiologically acceptable salts and hydrates), for the manufacture of a medicament for treating, relieving or preventing the effects of sexual dysfunction. Thus, the substituted acetic acid derivatives of formula (I) provided above may be used for the manufacture of a medicament for treating, relieving or preventing the effects of male sexual dysfunction, preferably erectile inadequacy and inhibited male orgasm, especially erectile inadequacy. The substituted acetic acid derivatives of the formula provided above may also be used for the manufacture of a medicament for treating, relieving or preventing the effects of female sexual dysfunction, preferably sexual arousal disorder and inhibited femal orgasm, especially sexual arousal disorder.

In a further embodiment, the present invention provides a method for the treatment of a male or female patient suffering from sexual dysfunction, or a method to prevent sexual dysfunction in a patient (having, for example, a history of sexual dysfunction) comprising the administration thereto of a therapeutically or prophylactically effective amount of a compound of formula (I), or a composition including same, as provided above. The sexual dysfunction may be, for example, male erectile dysfunction or impotence. A patient that cannot obtain an erection may be treated according to the present invention, while a patient that cannot maintain an erection may receive a prophylactic dose of a compound of the invention in order to prevent premature loss of an erection.

In a still further embodiment, the present invention provides a method for increasing the libido of a male or female patient comprising the administration thereto of a therapeutically effective amount of a compound of formula (I), or a composition including same, as provided above.

In a still further embodiment, the present invention provides a method for enhancing the sexual performance of a male or female patient that is not necessarily exhibiting symptoms of sexual dysfunction, comprising administering to the patient in need thereof a therapeutically or prophylactically effective amount of a compound of formula (I), or a composition including same, as provided above. Enhanced sexual performance occurs when there is an increase in the type of behavior that is typically associated with the patient's sexual activity or interest in sexual activity. Increased tone in the patient's genitals is one indication of an enhancement of sexual performance. Enhancement of sexual performance may result in, e.g., a pro-erectile response in the patient, or an improvement in erectile function such as any increase in the ability of the patient maintain an erection, induce or improve ejaculation (e.g., have multiple ejaculations within a shortened period of time), or induce or improve orgasm. Specific examples of enhancements in sexual performance are described in connection with the pharmacological testing of compounds and compositions of the present invention, as set forth herein.

The term "therapeutically effective amount" refers to an amount which is effective, upon single or multiple dose administration to the patient, to enhance the libido and/or sexual performance of the patient receiving the compound or a composition containing the compound as provided above. Such an amount may serve to treat a sexual dysfunction, e.g., impotence in males, and/or to enhance the sexual desire and/or sexual performance of a patient without a sexual dysfunction. For example, the therapeutically effective amount may be administered to, for example, a bull, to promote increased semen ejaculation, where the ejaculated semen is collected and stored for use as it is needed to impregnate female cows in promotion of a breeding program. Increased sexual ejaculation is an example of enhanced sexual performance according to the present invention.

A therapeutically or prophylactically effective amount of a substituted acetic acid derivative of the invention is expected to vary from about 0.01 milligram per kilogram of body weight per day (mg/kg/day) to about 200 mg/kg/day. Preferred amounts are expected to vary from about 0.5 to about 80 mg/kg/day. A pharmaceutical composition containing a substituted acetic acid derivative of the invention may contain between 0.01 and 1% by weight of the active substituted acetic acid derivative, and between about 5 and 10% by weight glucose in order to increase the osmolarity of the solution. Two illustrative compositions are (1) 5 mg/mL of a substituted acetic acid derivative of the invention and distilled water in 100 mL total volume, and (2) 5 mg/mL of a substituted acetic acid derivative of the invention, 25 mg/mL glucose, and distilled water in 100 mL total volume.

In effecting treatment of a patient in need of an agent for treating sexual dysfunction and/or enhancing sexual performance and/or a pro-libido agent, a compound of the invention can be administered in any form or mode which makes the compound bioavailable in effective amounts, including oral, aerosol, and parenteral routes. For example, compounds of the invention can be administered orally, by aerosolization, subcutaneously, intramuscularly, intravenously, transdermally, intranasally, rectally, topically, and the like. The compounds of the invention may be administered by direct injection into, e.g., the corpus cavernosa (intracavernously). The compounds of the invention may be administered intraurethrally (e.g., via an intraurethral catheter). The compounds of the invention may be administered topically, e.g., directly to the penis. The compounds may be administered intrameatally. Oral or aerosol administration is generally preferred. One skilled in the art of preparing formulations can readily select the proper form and mode of administration depending upon the particular characteristics of the compound selected, the condition to be treated, the stage of the condition, and other relevant circumstances. See, e.g., Remingtons's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice.

In another embodiment, the present invention provides compositions comprising a substituted acetic acid derivative of the invention in admixture or otherwise in association with one or more inert carriers. These compositions are useful, for example, as assay standards, as convenient means of making bulk shipments, or as pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001% to about 75% of the composition by weight. Inert carriers can be any material which does not degrade or otherwise covalently react with a compound of the invention. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a substituted acetic acid derivative as disclosed above, in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should preferably contain at least 4% of the compound of the invention as an active ingredient, but this amount may be varied depending upon the particular form and may conveniently be between 4% to about 70% of the weight of the unit. The amount of the compound present in compositions is such that a suitable dosage will be obtained. The tablets, pills, capsules and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but this amount may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 0.01 to 1% by weight of active compound.

The compounds of the present invention may also be administered by aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient. Delivery of the aerosol includes the necessary container, activators, valves, subcontainers, spacers and the like, which together may form a kit. Preferred aerosols are able to be determined by one skilled in the art.

The compounds of this invention may also be administered topically, and when done so the carrier may suitably comprise a solution, ointment or gel base. The base, for example, may comprise one or more of the following: petrolatum, lanolin, polyethylene glycols, beeswax, mineral oil, diluents such as water and alcohol, and emulsifiers and stabilizers. Topical formulations may contain a concentration of the inventive compound of from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred carrier or diluent.

The substituted acetic acid derivatives of the invention may be combined with one or more known pharmacological agents used in the treatment and/or prevention of sexual dysfunction and/or known to enhance the libido and/or sexual performance of a patient receiving the pharmacological agents.

The following examples are offered by way of illustration and not by way of limitation.

EXAMPLES

In the following Examples, unless otherwise indicated, the reactants, reagents and solvents were of standard commercial grade, and were obtained from Aldrich Chemical Co., Milwaukee, Wis., or a similar chemical supply house.

Example 1

Preparation of (±)-trans-N-methyl-[2-(1-(4-methyl) piperazinyl)cyclohexyl]naphthalene-1-acetamide monohydrochloride (XVa)

Acid chloride formation: 1-naphthylacetic acid (2.35 g, 12.6 mmol) was refluxed in thionyl chloride (10 mL) under nitrogen for 1 hour. After stirring at room temperature for a further two hours, the thionyl chloride was removed in vacuo to leave an oil which was dissolved in dichloromethane (10 mL).

Diamine formation: (±)-2-(1-(4-methyl)piperazino) cyclohexanol (15.0 g, 75.8 mmol) was added to triethylamine (11.4 mL, 81.8 mmol) and methylene chloride (100 mL) under nitrogen. The solution was cooled in an ice water bath to provide a cold solution of aminoalcohol. Methanesulfonyl chloride (6.4 mL, 82.7 mmol) and methylene chloride (40 mL) were added to the cold solution of aminoalcohol under nitrogen. The ice water bath was removed and the reaction mixture was stirred at room temperature for two hours. CG analysis showed that the reaction was essentially complete. The reaction mixture was partitioned between methylene chloride (100 mL) and water (100 mL). The aqueous phase was extracted with additional methylene chloride (50 mL). The methylene chloride extracts were combined, dried over sodium sulfate and the solvent removed in vacuo.

The isolated product (20.73 g) was dissolved in 50 mL (645 mmol) of methylamine solution (40 w/v in water) and heated to reflux for 2.5 hours. GC analysis of the reaction mixture showed that the displacement reaction was complete. The reaction mixture was partitioned between sodium hydroxide solution (140 mL, 10%) and methylene chloride. The aqueous phase was extracted with additional methylene chloride (85 mL). The methylene chloride extracts were combined and dried over sodium sulfate and the solvent removed in vacuo. The crude diamine (14.07 g) was a yellow oil. Vacuum distillation afforded a colorless liquid (12.08 g), which was (±)-2-(1-(4-methyl)piperazino) cyclohexyl-N-methylamine.

Amide formation: the acid chloride solution was added via cannula to a cooled (ice bath) solution of (±)-2-(1-(4-methyl)piperazino)cyclohexyl-N-methylamine (2.53 g, 12.0 mmol) in dichloromethane (10 mL) under nitrogen. The mixture was stirred at 0° C. for 15 min., then at room temperature for two hours. Ether (40 mL) was added slowly to the solution. A fine white solid precipitated. The mixture was stirred for 45 min., and then the solid product was filtered. The solid was rinsed with ether and dried in vacuo. The crude product (5.38 g) was recrystallized from hot methanol (300 mL). The solution was slowly cooled to the room temperature. Three crops of recrystallized product were collected, rinsed with ether, and dried in vacuo. The weight of the first crop was 3.5 g, the second 0.49 g, and the third 0.56 g. The three crops were combined and dissolved in hot methanol (275 mL). Product was recrystallized two times, rinsed in ether and dried in vacuo.

Microanalysis: C, 61.78; H, 7.82; N, 9.35; Cl, 15.83%; (theoretical for $C_{24}H_{35}N_3OCl_2$: C, 63.71; H, 7.80; N, 9.29; Cl, 15.67%).

Example 2

Preparation of (±)-trans-N-[2-(1-(4-methyl) piperazinyl)cyclohexyl]naphthalene-2-acetamide monohydrochloride (XVb)

Acid chloride formation: 2-naphthylacetic acid (2.23 g, 12.0 mmol) was refluxed in thionyl chloride (10 mL, 12.0 mmol) under nitrogen for 1 hour. The thionyl chloride was removed in vacuo (using 1×10 mL, 2×5 mL $CCl_4$) to leave a tan-colored solid, which was dissolved in dichloromethane (10 mL).

Azide formation: A flame-dried 2-necked round-bottomed flask was charged with sodium azide (14.8 g, 227 mmol) and DMF (50 mL). The mesylate of (±)-2-(1-(4-methyl) piperazino)cyclohexanol (15.17 g, prepared as in Example 1) was dissolved in dry DMF (100 mL) and added to the suspension of sodium azide via cannula. Additional DMF (20 mL) was added to the reaction mixture. The flask was fitted with a reflux condenser and the reaction mixture was warmed to 50° C. for 1.5 hours. The product mixture was partitioned between ether and water. The ether extract was analyzed by GC and found to contain no mesylate. The reaction mixture was stirred overnight at room temperature under nitrogen. Then diethyl ether (250 mL) was added and the combination washed with water (100 mL). The aqueous DMF phase had a red/brown color while the ether phase was yellow. The ether layer was washed with additional water (2×20 mL) and then dried over sodium sulfate. Upon removal of the solvent in vacuo, the residue (±)-trans-2-(1-(4-methyl)piperazino)cyclohexylazide weighed 12.37 g.

Diamine formation: (±)-trans-2-(1-(4-methyl)piperazino) cyclohexylazide (12.37 g, 55.5 mmol) was dissolved in a solution of 4:1 methanol:glacial acetic acid (55 mL). Palladium on charcoal (2.1 g) was added to the solution and the mixture became warm. The mixture was placed into a high pressure bomb, and the bomb placed into a bath of liquid nitrogen until the contents were frozen. The bomb was evacuated, then charged with hydrogen gas and sealed, all while maintaining the bomb contents in a frozen state. The reaction mixture was removed from the liquid nitrogen bath and was warmed to room temperature, stirred for 4 days, dried and filtered. GC analysis showed that the content of the mixture was 60:40 aminocyclohexylpiperazine:azide starting material. The reaction mixture was again placed under a hydrogen atmosphere, according to the procedure described above, and then warmed to room temperature and stirred for two days. GC analysis failed to identify any azide in the reaction mixture. The reaction mixture was filtered and rinsed with a solution of 4:1 methanol:glacial acetic acid and dried in vacuo. Acetic acid (100 mL, 10%) was added to the concentrate, and the pH was lowered to 1 by adding 6N HCl. The acidic aqueous layer was extracted with methylene chloride (3×50 mL), and the methylene chloride extracts were discarded. The aqueous layer was basified to pH 12 by addition of 50% sodium hydroxide solution and then extracted with methylene chloride (4×50 mL). The methylene chloride extracts were combined and dried over sodium sulfate and the solvent was then removed in vacuo. The weight of the crude product was 10.65 g. Vacuum distillation afforded a colorless solid distillate, 8.48 g, m.p. 78–79° C., which is (±)-trans-2-(1-(4-methyl)piperazino) cyclohexylamine.

Amide formation: The acid chloride solution was added via cannula to a room temperature solution of (±)-trans-2-(1-(4-methyl)piperazino)cyclohexylamine (2.25 g, 11.4 mmol) in dichloromethane (10 mL) under nitrogen. The mixture was stirred at room temperature for 1 hour. A fine white precipitate formed. Ether (50 mL) was added slowly to the mixture to complete precipitation of a solid which was filtered and rinsed with ether (3×15 mL). The crude product (4.63 g) was recrystallized from hot ethyl acetate (60 mL)/hot methanol (20 mL). The solution was slowly cooled to room temperature to give three crops of crystalline product which were collected, rinsed with ether and dried in vacuo. Weight of the first crop was 3 g, the second crop 0.6 g, the third crop 1.15 g.

Microanalysis: C, 68.97; H, 7.94; N, 10.81%; (theoretical for $C_{22}H_{32}N_3OCl$: C, 68.72; H, 8.02; N, 10.45%).

Example 3

Preparation of (±)-trans-[2-(1-(4-methyl) piperazinyl)cyclohexyl]naphthalene-1-acetate monohydrochloride (XVc)

Acid chloride formation: 1-naphthylacetic acid (2.47 g, 13.3 mmol) was refluxed in thionyl chloride (10 mL) under nitrogen for 1 hour. The mixture was stirred at room temperature for a further 3 hours before the thionyl chloride was removed in vacuo (using 1×10 mL, 2×5 mL $CCl_4$). The residue was dissolved in chloroform (10 mL).

Ester formation: the acid chloride solution was added via cannula to a room temperature solution of (±)-trans-2-[1-(4-methyl)piperazino]cyclohexanol (2.51 g, 12.6 mmol, "starting aminoalcohol") in chloroform (10 mL) under nitrogen. The reaction was refluxed for 2.5 hours, at which time GC analysis showed a mixture (2:1 ester:starting aminoalcohol) of products. Accordingly, the reaction mixture was refluxed for an additional 16 hours before removal of the solvent in vacuo. The residue was partitioned between HCl solution (100 mL, 1M) and ether (60 mL). The aqueous phase was extracted with additional ether (2×30 mL). The aqueous layer was basified to pH 12 by addition of 50% NaOH solution. The basic aqueous phase was extracted with ether (1×60 mL, 2×40 mL) and the ether extracts were combined and washed with water (2×100 mL, 2×75 mL, 2×50 mL, 16×25 mL) to remove any aminoalcohol. GC analysis showed that the ether extract contained 1.5% starting aminoalcohol impurity. The ether extract was dried over sodium sulfate and the solvent was removed in vacuo.

The isolated product (3.24 g) was dissolved in ether (20 mL) and treated with a solution of HCl in ether. A fine precipitate was formed. The solid was filtered and rinsed with ether (3×10 mL). The salt was dried in vacuo. The crude HCl salt was recrystallized from hot methanol (10 mL). Two small crops of recrystallized product were collected. Weight of the first crop was 0.59 g, the second crop 0.14 g. The mother liquor was evaporated to dryness and the residue was dissolved in hot ethyl acetate (40 mL)/hot ethanol (3 mL). A third crop of ester was collected and combined with the first two crops. The combined first, second and third crops were pumped on the vacuum line for 3 hours. A fourth crop of product was collected as above. Microanalysis indicated that the salt contained 1.6 equivalent of HCl.

All four crops of salt were combined and dissolved in warm methanol (30 mL) and to this was added a solution of HCl in methanol to produce a fine white precipitate. Two crops of dihydrochloride salt were collected, rinsed with ether (3×10 mL) and dried in vacuo. These two crops were recrystallized from hot ethyl acetate (40 mL)/hot methanol (60 mL). The recrystallized dihydrochloride salt (1.78 g) was filtered off, rinsed with ether (3×10 mL) and dried in vacuo. The dihydrochloride (di-HCl) salt did not dissolve in $D_2O$.

The mother liquor from the ethyl acetate/methanol recrystallization was evaporated and the residue was mixed with the isolated di-HCl salt. This mixture was partitioned between 1M NaOH solution (80 mL) and dichloromethane (80 mL). The aqueous phase was further extracted with dichloromethane (1×50 mL, 1×30 mL). The organic extracts were combined, dried over sodium sulfate and concentrated in vacuo. The residual free ester (2.20 g) was pumped on the vacuum line. The free ester was dissolved in dichloromethane:ether (1:6, 84 mL). One equivalent of HCl in dichloromethane:ether (1:6) was added dropwise, with stirring, to the ester solution over a period of 6–8 hours. A fine white solid precipitated from the solution. The solid was filtered off and washed with ether (3×10 mL). The monohydrochloride salt (2.09 g) was dissolved in hot ethyl acetate (30 mL)/hot methanol (10 mL). The solution was slowly cooled to room temperature. Two crops of recrystallized monohydrochloride salt were collected and combined. This product was rinsed with ether and dried in vacuo.

Microanalysis: C, 67.33; H, 7.52; N, 6.91%; (theoretical for $C_{23}H_{31}N_2O_2Cl$: C, 68.56; H, 7.75; N, 6.95%).

Example 4A

Preparation of 1-Methyl-4(1-naphthaleneacetyl) piperazine monohydrochloride (XVIa)

Acid Chloride formation: 1-naphthylacetic acid (5.00 g, 26.8 mmol) was refluxed in thionyl chloride (10 mL) under nitrogen for 1 hour. The mixture was stirred at room temperature for a further 1 hour, and the thionyl chloride was removed in vacuo (using 1×10 mL, 2×5 mL $CCl_4$) to leave an oil which was dissolved in dichloromethane (50 mL).

Amide formation: The acid chloride solution was added via cannula to a cooled (−78° C.) solution of 1-methylpiperazine (2.69 g, 26.8 mmol) in dichloromethane (50 mL) under nitrogen. The resulting thick white suspension was filtered and washed with ether (3×10 mL) and dried to provide a first crop (3.06 g). A second crop (1.05 g) was collected from the filtrate.

Microanalysis: C, 66.30; H, 6.96; N, 9.13%; (theoretical for $C_{17}H_{21}N_2OCl$: C, 66.99; H, 6.94; N, 9.19%).

Example 4B

Preparation of 1-Methyl-4(2-naphthaleneacetyl) piperazine monohydrochloride (XVIb)

Acid chloride formation: 2-naphthylacetic acid (3.90 g, 21.0 mmol) was refluxed in thionyl chloride (10 mL) under nitrogen for 1 hour. The mixture was stirred at room temperature for a further 1.5 hour before the thionyl chloride was removed in vacuo (using 1×10 mL, 2×5 mL $CCl_4$). The residue, an orange solid, was dissolved in dichloromethane (7 mL).

Amide formation: The acid chloride solution was added via cannula to a cooled (ice bath) solution of 1-methylpiperazine (2.0 g, 20 mmol) in dichloromethane (10 mL) under nitrogen. Additional dichloromethane (25 mL) was added in order to reduce the viscosity of the reaction medium since a great deal of white solid precipitated from solution almost immediately. The mixture was stirred at room temperature for 30 min. The crude product (5.44 g) was filtered off and washed with ether (3×15 mL). The product was pumped on the vacuum line then dissolved in hot methanol. Further cooling (slowly) provided a solid precipitate (3.19 g). The product was filtered, washed with ether and dried in vacuo.

Microanalysis: C, 66.60; H, 7.27; N, 9.12%; (theoretical for $C_{17}H_{21}N_2OCl(0.5\ H_2O)$: C, 65.06; H, 7.07; N, 8.93%).

Example 5A

Preparation of 1-Methyl-4-(2-(3,4-Dichlorophenyl) acetyl)piperazine Monohydrochloride (XVIIa)

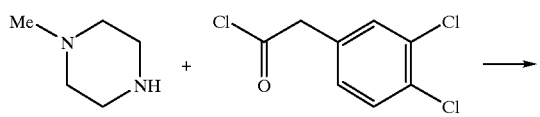

-continued

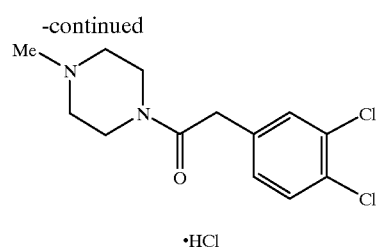

·HCl

Acid chloride formation: 3,4-Dichlorophenyl acetic acid (5.13 g, 25.0 mmol) was refluxed in thionyl chloride (13 mL) under argon for 1 h. After stirring at room temperature for a further 30 minutes, the excess thionyl chloride was removed in vacuo (using 3×5 mL $CCl_4$). The residue, an orange oil, was dissolved in dichloromethane (25 mL).

Amide formation: To the acid chloride solution cooled with ice-water bath was added through a syringe a solution of 1-methylpiperazine (2.66 mL, 24.0 mmol) in dichloromethane (15 mL) under argon. The mixture then became a thick suspension which was stirred at 0° C. for 10 min and at room temperature for 1 h. The crude product (7.56 g) was filtered off, washed with dichloromethane (10 mL) and ether (2×20 mL), and dried on the high vacuum line for 30 min. The crude product was recrystallized in hot methanol (15 mL)/acetone (30 mL)/ether (25 mL). Crop #1 (4.99 g, white crystal) was collected, washed with acetone/ether (1:3 v/v, 2×15 mL) and dried in vacuo. Crop #2 (1.26 g, pale yellow powder) was collected from the concentrated mother liquor.

$^{13}C$ NMR of Crop #1: (75 MHz, $D_2O$) δ: 171.56 (CO); 135.23, 131.89, 131.51, 130.75, 130.66, 129.61 (aromatic); 53.07 ($\underline{C}H_2NCH_3$); 43.21 ($NCH_3$); 43.0, 39.31 ($\underline{C}H_2NCO$); 38.51 ($\underline{C}H_2CO$)

Example 5B

Preparation of 1-Methyl-4-(3,4-Dimethoxyacetyl) Piperazine Monohydrochloride (XVIIB)

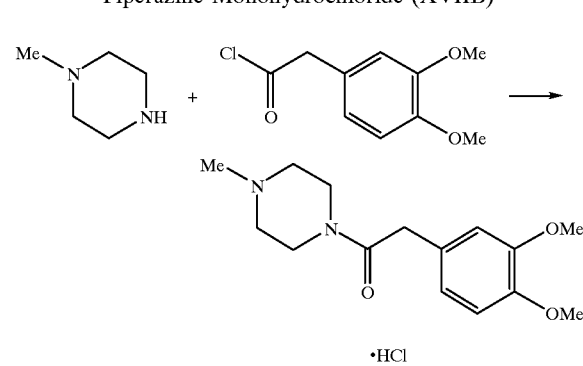

·HCl

Acid chloride formation: 3,4-Dimethoxyphenyl acetic acid (5.0 g, 25.5 mmol) was refluxed in thionyl chloride (14.7 mL) under argon for 1 h. After stirring at room temperature for a further 30 minutes, the thionyl chloride was removed in vacuo (using 1×10, 2×5 mL $CCl_4$). The residue, a dark red oil, was dissolved in dichloromethane (7 mL).

Amide formation: the acid chloride solution was added to a cooled (ice bath) solution of 1-methylpiperazine (2.42 g, 24.2 mmol) in dichloromethane (10 mL) under argon. Additional dichloromethane (25 mL) was added in order to allow the reaction to stir (a great deal of white solid precipitated from solution almost immediately). The mixture was stirred at room temperature for 30 min. The crude product was filtered off and washed with ether (3×15 mL). The product was pumped on the vacuum line then recrystallized in toluene/ethanol. The flaky crystal was filtered and washed with ether and dried in vacuo to yield a white solid (5.0 g).

$^{13}$C NMR: (75 MHz, $D_2O$) δ: 172.93 (CO), 148.4, 147.4, 127.4, 121.8, 112.8, 112.1 (aromatic); 55.8 ($OCH_3$), 53.0 ($NCH_2$), 43.1 ($NCH_3$), 39.2 ($CONCH_2$), 39.0 ($COCH_2$)

Pharmacological Testing

Example 6

Effect of N-Methylpiperazine Acetic Acid Compounds on Sexual Behavior in Male Primates (Paired Observation Study)

Adult *macaca fascilaris* (3.8–8 kg; n=6) were given by injection (1.0 mg/kg; ip; 0.5 mL/kg body weight) saline and/or solutions of compounds XVa, XVb, XVc, XVIa and XVIb, and their behavioral responses were observed for 1 hour following a 10 min. delay for drug distribution. Monkeys used for testing were separated from the cluster of cages and treated and observed in pairs in the middle of the housing environment. Test compounds were randomized such that one monkey received test compound and the other received saline in each pair, although the observers did not know which was the drug-treated animal.

The results are provided in Table 1. N=3 for all drug-treated animals, while N=18 for saline-treated animals. Table 1 indicates the sexual response of test animals exhibiting erection. Data are expressed as the number of test animals having a particular grade of penile response. Penile responses were scored every 10 sec for 1 hour according to the following scale:

Grade 0=glans are hidden from the view

Grade 1=glans are clearly visible

Grade 2=penis is extended

Grade 3=full erection

Grade 4=erection with masturbation

Grade 5=erection with masturbation and ejaculation

TABLE 1

EFFECT OF N-METHYLPIPERAZINES OF ACETIC COMPOUNDS ON SEXUAL BEHAVIOR IN MALE PRIMATES

| Compound | XVa | XVb | XVc | XVIa | XVIb | Saline |
|---|---|---|---|---|---|---|
| Grade 0 | 1 | 1 | 1 | 1 | 1 | 12 |
| Grade 1 | 2 | 2 | 2 | 2 | 2 | 6 |
| Grade 2 | 2 | 2 | 2 | 2 | 2 | 4 |
| Grade 3 | 2 | 1 | 2 | 1 | 2 | 1 |
| Grade 4 | 2 | 0 | 2 | 1 | 1 | 1 |
| Grade 5 | 0 | 0 | 1 | 0 | 0 | 1 |

Example 7

Direct Action on Penile Erection

Corpus cavernosal (CC) muscle strips were prepared from penises obtained from rabbit (n=6). CC strips were dissected free from tunica albungia and mounted in 10 or 25 mL organ baths containing Tyrode solution saturated with 95%$O_2$/5% $CO_2$ mixture. Compound XVIb and 1-methyl-4-trifluoromethylphenylpiperazine (variation of concentration from $10^{-8}$ M to $10^{-4}$ M) failed to reduce tone in noradrenaline pre-contracted rabbit CC, whereas Trazodone reduced tone of rabbit CC in a dose dependent manner.

Example 8A

Effects of Compounds XVI(a,b) on Rat Sexual Behavior (Proerectile actions)

Male SD rats (350–450 g; n=10 per group) were injected with increasing doses of XVIb (4.0–64.0 mg/kg), XVIa (1.0, 4.0 or 16 mg/kg) or saline and observed 5 minutes later, in groups of 5, for the number of erections and the time to the first erection, over a 60 minutes observation period.

XVIb produced erections in rats in a bell shaped dose-response fashion (Table 2). The maximal effect of XVIb was observed at 16 mg/kg. Latency to the first erection was effected in a "U" shaped dose response fashion with minimal time to the first erection also occurring at a dose of 16 mg/kg. At doses greater than 16 mg/kg the number of erections/rat was diminished whereas the number of responders was not reduced. Latency to the first erection was also increased at doses greater than 16 mg/kg. XVIa also increased penile erections, although to a lesser degree than XVIb.

In Table 2, the effects of XVIb, XVIa and saline on erection in male rats is indicated. Data is expressed as the mean±sem for 10 test animals. Data marked with an asterisk "*" indicate significant difference from saline ($\alpha<0.05$) as determined by ANOVA with Tukey test for multiple comparisons.

TABLE 2

EFFECT OF COMPOUNDS XVIA, XVIB AND SALINE ON ERECTILE RESPONSES IN MALE RATS.

| Drug (mg/kg) | Erections/ 60 minutes (#) | Latency to the first erection (sec) | Responders (%) |
|---|---|---|---|
| XVIb (4.0) | 2.1 ± 0.4 | 2390 ± 238 | 100 |
| XVIb (8.0) | 5.1 ± 0.6* | 1299 ± 214 | 100 |
| XVIb (16.0) | 7.7 ± 0.4* | 654 ± 108* | 100 |
| XVIb (32.0) | 2.5 ± 0.2 | 1046 ± 64* | 100 |
| XVIb (64.0) | 2.7 ± 0.5 | 3319 ± 170* | 100 |
| XVIa (1.0) | 1.2 ± 0.3 | 1929 ± 432 | 100 |
| XVIa (4.0) | 3.0 ± 0.6 | 1749 ± 349 | 100 |
| XVIa (16.0) | 5.4 ± 0.7* | 506 ± 105* | 100 |
| Saline | 1.2 ± 0.4 | 2010 ± 334 | 40 |

Example 8B

Effects of Compound XVIb Administered Orally on Rat Sexual Behavior (Proerectile Actions)

Male SD rats (250–300 g) were administered increasing doses of XVIb (30–100 mg/kg in distilled water, per os) or distilled water only via a feeding tube, and observed 5 minutes later for the number of erections (as characterized by penile grooming) over a 60 minute observation period. Six rats at a time, housed singly, were observed by two observers. Treatments were administered in a standard randomized and double blinded manner.

XVIb produced erections in rats after oral administration. The effect of XVIb was dose dependent. At a dose of 30 mg/kg p.o. the maximum number of erections/rat was 3/hr, whereas at 100 mg/kg p.o. the maximum number of erections/rat was 5/hr, with 100% responders in both drug groups. In the control rats the maximum number of erections per rat was 1/hr and with only 50% responders.

Example 8C

Effects of Compounds XVIIa and XVIIb on Rat Sexual Behavior (Proerectile Actions)

Male SD rats (250–300 g) were injected with XVIIa (16 mg/kg, ip), XVIIb (16 mg/kg, ip) or distilled water (ip), and observed 5 minutes later for the number of erections (as characterized by penile grooming) and the time to the first erection, over a 60 minute observation period. Six rats at a time, housed singly, were observed by two observers. Treatments were administered in a standard randomized and double blinded manner.

At the dosage used (16 mg/kg), the maximum number of erections/rat was 3/hr and the latency to first erection was 6 min for XVIIa with 67% responders; while for XVIIb the maximum number of erections/rat was 5/hr and the latency to first erection was 16 min with 100% responders. In the control rats the maximum number of erections per rat was 1/hr and latency to first erection was 21 min with only 50% responders.

Example 9

Effects of Compound XVIb on Rat Behavior, Blood Chemistry and Body Temperature Male SD rats (350–450 g; n=15 per group) were injected with a single dose of XVIb (16 mg/kg, ip) and saline and observed 5 minutes later, in pairs, for erections, ejaculation, movement and grooming over a 60 minute observation period. Rectal temperature was recorded before drug administration and 1 hour after drug administration. At the end of experiments rats were decapitated and trunk blood was collected for RIA analysis of serum cortisol and prolactin levels.

At a dose of 16 mg/kg of compound XVIb, erections and ejaculations were significantly increased compared to saline control (XVIb 5.6±0.7 erections/60 minutes versus saline, 1.3±0.3 erections/60 minutes; XVIb, 1.8±0.1 ejaculations versus saline, 0.2±0.1 ejaculations; p<0.001). At this dose, XVIb significantly increased penile grooming (XVIb, 12.1±3.3 grooms/60 minutes versus saline, 7.4±2.1 grooms/60 minutes; p<0.01) but had no effect on non-penile grooming (XVIb, 22±4.8 grooms/60 minutes versus saline 21.3±3.4 grooms/60 minutes; p>0.5). Rearing (XVIb, 77±5.9 rears/60 minutes; p>0.3 ) and locomotion (XVIb, 20.7±3.3 moves versus saline, 28.4±4.6 moves; p>0.4) were not significantly affected at this dose. Serum prolactin and cortisol were not significantly altered. Rectal temperature was not significantly altered by XVIb at 16 mg/kg.

Example 10

Effects of Compound XVIb vs. Comparative Compounds on Rat Behavior

Male SD rats (300–500 g; n=6 per group) were injected with (±)-Pindolol, scopolamine, haloperidol, or ketanserin, 30 minutes prior to injection of a single dose of XVIb (16 mg/kg, ip) or saline. 5 minutes later animals were observed for the occurrence of erection over a 60 minute observation period.

(±)-Pindolol (0.1–3 mg/kg) and scopolamine (0.1–3.0 mg/kg), but not haloperidol (0.01–0.3 mg/kg) and ketanserin (0.1–3.0 mg/kg), antagonized the erectile promoting actions of an optimal dose of XVIb (16 mg/kg). At the highest dose tested, (±)-pindolol reduced erection from 7.8±1.4 erections/60 minutes to 2.0±0.4 erections/60 minutes (p <0.05). Scopolamine reduced erections from 1.7 erections/60 minutes to 1.2±0.3 erections/60 minutes(p<0.05).

Example 11

Effects of Compound XVIb on Rat Procopulatory Actions

Male Long-Evans rats (300–600 g; n=15 per group) were injected with saline or XVIb (1.5–30.5 mg/kg; ip) 5 minutes prior to being paired with a female rat sexually receptive by administration of estradiol benzoate (25 $\mu$g; 48 hours prior to testing) and progesterone (1 mg/kg; 4 hours prior to testing). Mount latency, intromission latency, ejaculation latency, mounts, intromissions, ejaculations and post ejaculatory interval were recorded over a 30 minutes observation period.

Mount latency and intromission were not significantly affected at dose of 15 mg/kg despite an obvious trend for a reduction in both latency's. Ejaculation latency, the number of ejaculations and the number of intromissions were all affected significantly at a dose of 15 mg /kg (Table 3). Post ejaculatory interval was not affected at any of doses tested. At doses above and below 15 mg/kg, compound XVIb was without significant effects on copulatory behaviors other than reducing the number of intromissions (7.5 mg/kg and 30.5 mg/kg only; data is not shown).

In Table 3, the effect of compound XVIb on copulatory behavior in male rats is shown. Data are expressed as mean (sem for 15 test animals). Latency is the time in seconds to appearance of that behavior. Ejaculations are the number of such events during 30 minutes of observation. Intromissions are the number of such events before ejaculation. Post ejaculatory interval is the time in seconds from ejaculation on intromission to the first mount of the next copulatory sequence. P values derived from two-tailed t-test for significance between mean values ($\alpha$<0.05).

TABLE 3

EFFECTS OF COMPOUND XVIB ON MALE RAT COPULATORY BEHAVIOR.

| Behavior | XVIb (15 mg/kg) | Saline | Significance versus saline. |
|---|---|---|---|
| Mount latency (sec) | 204.5 ± 31.9 | 156.6 ± 21.13 | p > 0.2 |
| Intromission latency (sec) | 405.1 ± 88.0 | 246.8 ± 38.0 | p > 0.1 |
| Ejaculation latency (sec) | 330.9 ± 31.5 | 415.5 ± 28.0 | p < 0.05 |
| Ejaculations (#) | 4.7 ± 0.2 | 4.2 ± 0.1 | p < 0.05 |
| Intromissions (#) | 6.9 ± 0.7 | 9.1 ± 0.5 | p < 0.05 |
| Post ejaculatory interval (sec) | 426.6 ± 28.5 | 446.8 ± 26.7 | p > 0.8 |

Example 12

Effects of Compound XVIb on Primate Sexual Behavior (Isolated Observation Study)

Adult male Macaca fascilaris (3.8–8 kg, n=6) were injected (0.1–10.0 mg/kg; ip; 0.5 mL/kg body weight) with either saline or compound XVIb and observed 10 minutes later for behavioral responses and locomotion for 1 hour. Monkeys used for testing were injected and observed in separate locations remote from housing environment. Each monkey received a dose of XVIb at 72 hour intervals.

XVIb dose dependently (0.1–10 mg/kg) increased grade 1 penile erections in primates observed in isolation. However this effect reached significance only at the highest dose tested. Advanced grades of penile erection (grades 2–5) were not significantly affected at any dose (Table 4). At the highest dose tested, indicators of purse lip gestures but not yawning were significantly increased (Table 4).

In Table 4, the effect of compound XVIb on erectile responses is reported for male primates observed in isolation. Data are expressed as mean (sem, standard error of measurements) for 6 test animals. Penile responses were scored every 10 seconds for 1 hour according to the following scale: Grade 0=glans hidden from view, Grade 1=glans clearly visible, Grade 2=penis extended, Grade 3=full erection, Grade 4=erection with masturbation, Grade 5=erection with masturbation and ejaculation. In Table 4, data marked with an asterisk "*" indicate a significant difference from saline as determined by repeated measures ANOVA and Dunnetts test for multiple comparisons ($\alpha<0.05$). The data in Table 4 are reported as % genital observations.

TABLE 4

EFFECT OF COMPOUND XVIB ON MALE PRIMATE ERECTILE RESPONSES. (ISOLATED OBSERVATION STUDY)

| Response Treatment (mg/kg) | Grade 0 | Grade 1 | Grade 2 | Grade 3 | Grade 4 | Grade 5 | # of behavioral Purse Lip Gesture | Yawning |
|---|---|---|---|---|---|---|---|---|
| XVIb | | | | | | | | |
| (0.1) | 81.8 ± 8.2 | 17.8 ± 7.9 | 0.4 ± 0.3 | 0 ± 0 | 0 ± 0 | 0 ± 0 | 5.8 ± 3.9 | 8.8 ± 4.5 |
| (0.3) | 67.3 ± 12.2 | 32.8 ± 11.5 | 0.5 ± 0.5 | 0 ± 0 | 0 ± 0 | 0 ± 0 | 10.2 ± 3.9 | 11.7 ± 3.8 |
| (1.0) | 72.0 ± 12.0 | 26.6 ± 10.6 | 1.4 ± 1.4 | 0 ± 0 | 0 ± 0 | 0 ± 0 | 7.5 ± 3.4 | 11.3 ± 2.5 |
| (3.0) | 56.8 ± 7.8 | 42.1 ± 8.3 | 1.7 ± 1.4 | 0.3 ± 0.3 | 0 ± 0 | 0 ± 0 | 14.0 ± 8.3 | 13 ± 3.4 |
| (10.0) | 24.5 ± 7.6 | 72.1 ± 7.7* | 2.5 ± 1.0 | 0.9 ± 0.6 | 0 ± 0 | 0 ± 0 | 33 ± 14* | 14.0 ± 4.0 |
| Saline | 68.7 ± 11.8 | 31.3 ± 11.8 | 0 ± 0 | 0 ± 0 | 0 ± 0 | 0 ± 0 | 6.5 ± 4.5 | 8.2 ± 2.7 |

Example 13

Toxicity Studies

A compound of the present invention was orally administered to rat, and the rat showed no overt sign of adverse acute toxicity at a dose of up to 100 mg/kg (p.o.). When tested in mouse, the following $LD_{50}$ values were obtained for the compound: 318 mg/kg (subcutaneous); 194 mg/kg (intraperitoneal); 87 mg/kg (intravenous) and 450 mg/kg (oral).

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for treating or preventing sexual dysfunction in a patient, comprising administering to the patient in need thereof an amount of a compound of the formula

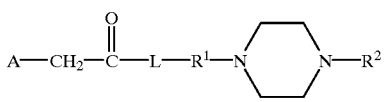

including salts, solvates, isolated enantiomers, isolated diastereomers, isolated tautomers, and mixtures thereof, wherein, independently at each occurrence:

Ar is selected from a $C_3$–$C_{13}$carbocyclic ring, and ring systems selected from formulae (II), (III), (IV), (V), (VI), and (VII):

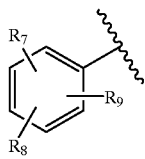

(II)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and N($R_{15}$,$R_{16}$) where $R_{15}$ and $R_{16}$ are independently selected from hydrogen, acetyl, methanesulfonyl, and $C_1$–$C_6$alkyl;

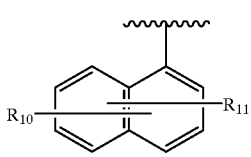

(III)

and (IV)

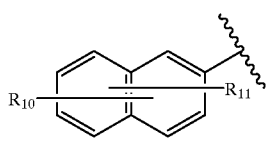

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

(V)

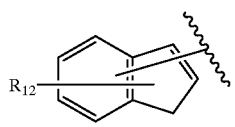

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and (VI)

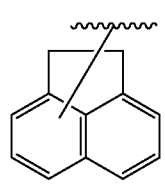

(VII)

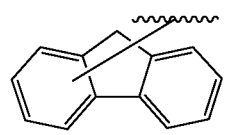

including isolated enantiomeric, diastereomeric, tautomeric and geometric isomers thereof, and mixtures thereof;

L is a direct bond;

$R^1$ is selected from the group of a direct bond, a $C_1$–$C_6$ alkylene group, and a 1,2-disubstituted $C_5$–$C_6$ cycloalkyl; and $R^2$ is $C_1$–$C_6$ alkyl;

where the amount is effective to treat or prevent the sexual dysfunction of the patient.

2. The method of claim 1 wherein the sexual dysfunction is male erectile dysfunction.

3. The method of claim 1 wherein the sexual dysfunction is impotence.

4. A method for increasing the libido of a male or female patient, comprising administering to the patient in need thereof an amount of a compound of the formula

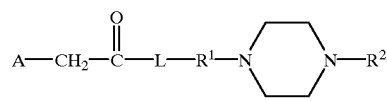

including salts, solvates, isolated enantiomers, isolated diastereomers, isolated tautomers, and mixtures thereof, wherein, independently at each occurrence:

Ar is selected from a $C_3$–$C_{13}$carbocyclic ring, and ring systems selected from formulae (II), (III), (IV), (V), (VI), and (VII):

(II)

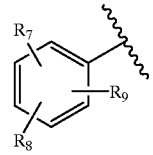

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl;

(III)

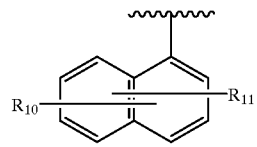

and (IV)

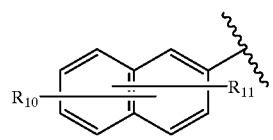

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

(V)

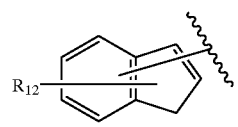

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and (VI)

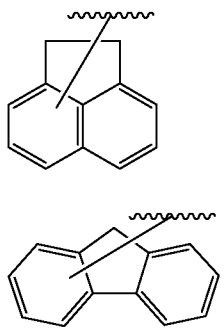

(VII)

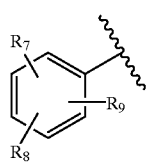

including isolated enantiomeric, diastereomeric, tautomeric and geometric isomers thereof, and mixtures thereof;

L is a direct bond;

$R^1$ is selected from the group of a direct bond, a $C_1$–$C_6$ alkylene group, and a 1,2-disubstituted $C_5$–$C_6$ cycloalkyl; and $R^2$ is $C_1$–$C_6$ alkyl;

where the amount is effective to increase the libido of the patient.

5. A method for enhancing the sexual performance of a male or female patient, comprising administering to the patient in need thereof an amount of a compound of the formula

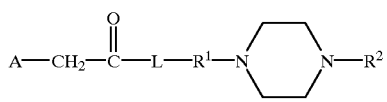

including salts, solvates, isolated enantiomers, isolated diastereomers, and mixtures thereof, wherein, independently at each occurrence:

Ar is selected from a $C_3$–$C_{13}$carbocyclic ring, and ring systems selected from formulae (II), (III), (IV), (V), (VI), and (VII):

(II)

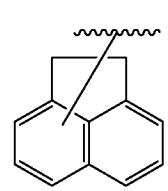

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl;

(III)

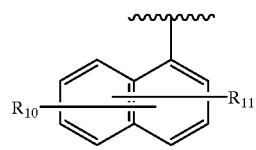

and (IV)

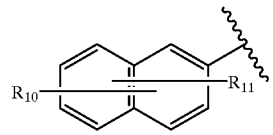

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

(V)

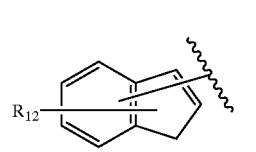

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and (VI)

(VII)

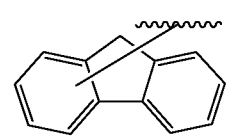

including isolated enantiomeric, diastereomeric, tautomeric and geometric isomers thereof, and mixtures thereof;

L is a direct bond;

$R^1$ is selected from the group of a direct bond, a $C_1$–$C_6$ alkylene group, and a 1,2-disubstituted $C_5$–$C_6$ cycloalkyl; and $R^2$ is $C_1$–$C_6$ alkyl;

where the amount is effective to enhance the sexual performance of the patient.

6. The method of claim 5 wherein the compound provides a pro-erectile response in the patient.

7. The method of claim 1, 4 or 5 wherein $R^1$ is a direct bond.

8. The method of claim 1, 4 or 5 wherein the compound has the formula

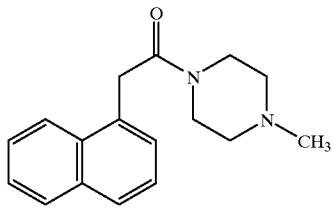

including salts, solvates, isolated tautomers, and mixtures thereof.

9. The method of claim 1, 4 or 5 wherein the compound has the formula

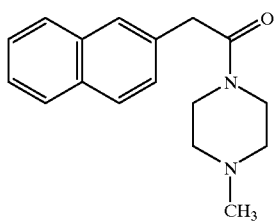

including salts, solvates, isolated tautomers, and mixtures thereof.

10. The method of claim 1, 4 or 5 wherein the compound has one of the formulae

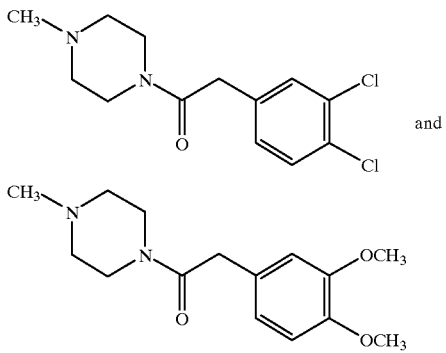

and including salts, solvates, isolated tautomers, and mixtures thereof.

11. The method of claim 1, 4 or 5 wherein $R^1$ is 1,2-disubstituted cyclohexane.

12. The method of claim 1, 4 or 5 wherein the administration is by oral administration.

13. The method of claim 1, 4 or 5 wherein the administration is by topical administration.

14. The method of claim 1, 4 or 5 wherein the administration is by direct injection.

15. The method of claim 1, 4 or 5 wherein the administration is by one of intrameatal, intracavernous and intraurethral.

* * * * *

UNITED STATES PATENT AND TRADEMARK OFFICE
CERTIFICATE OF CORRECTION

PATENT NO. : 6,399,618 B1
DATED : June 4, 2002
INVENTOR(S) : Alexander B. Zolotoy et al.

It is certified that error appears in the above-identified patent and that said Letters Patent is hereby corrected as shown below:

Column 34,
Line 1, the following formula:

"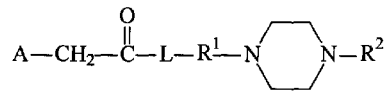"

should be corrected to read

-- 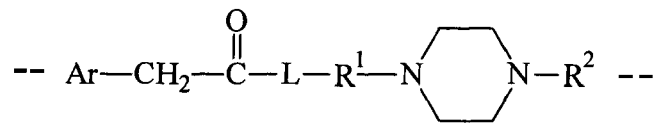 --

Column 36,
Line 1, the following formula:

"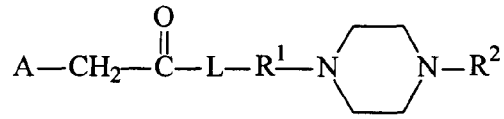"

should be corrected to read

-- 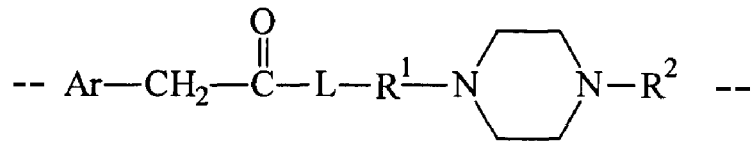 --

UNITED STATES PATENT AND TRADEMARK OFFICE
CERTIFICATE OF CORRECTION

PATENT NO. : 6,399,618 B1
DATED : June 4, 2002
INVENTOR(S) : Alexander B. Zolotoy et al.

It is certified that error appears in the above-identified patent and that said Letters Patent is hereby corrected as shown below:

Column 37,
Line 39, the following formula:

"                                                                                                      "

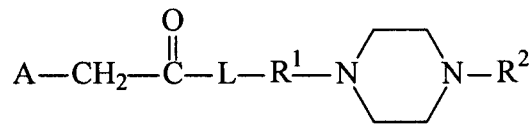

should be corrected to read

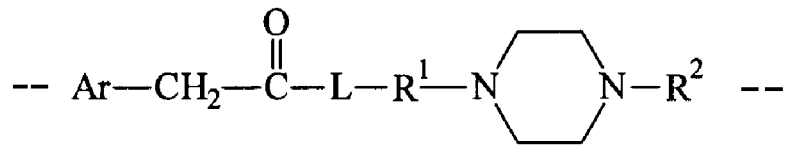

Signed and Sealed this

Twelfth Day of November, 2002

*Attest:*

JAMES E. ROGAN
*Director of the United States Patent and Trademark Office*

*Attesting Officer*